United States Patent [19]
Walch et al.

[11] Patent Number: 5,702,457
[45] Date of Patent: Dec. 30, 1997

[54] HUMERAL PROSTHESIS INCORPORATING A SPHERE

[75] Inventors: Gilles Walch, Lyons; Pascal Boileau, Nice, both of France

[73] Assignee: Tornier SA, Saint-Ismier, France

[21] Appl. No.: 557,323

[22] Filed: Nov. 14, 1995

[30] Foreign Application Priority Data

Nov. 18, 1994 [FR] France .................... 94 14052

[51] Int. Cl.$^6$ .................................................. A61F 2/40
[52] U.S. Cl. .................................................. 623/19; 623/23
[58] Field of Search ........................ 623/19, 23, 18, 623/22, 20; 606/62, 67, 95

[56] References Cited

U.S. PATENT DOCUMENTS

| | | | |
|---|---|---|---|
| 3,889,299 | 6/1975 | Osborne et al. | 623/23 |
| 3,916,451 | 11/1975 | Buechel et al. | 623/19 X |
| 4,106,128 | 8/1978 | Greenwald et al. | |
| 4,179,758 | 12/1979 | Gristina | 623/19 X |
| 4,459,708 | 7/1984 | Buttazzoni | 623/18 |
| 4,731,088 | 3/1988 | Collier | 623/22 |
| 4,846,840 | 7/1989 | Leclercq et al. | 623/23 |
| 4,908,036 | 3/1990 | Link et al. | 623/23 |
| 5,358,526 | 10/1994 | Tornier . | |

FOREIGN PATENT DOCUMENTS

| | | | |
|---|---|---|---|
| 2689756 | 10/1993 | France . | |
| 2697996 | 5/1994 | France . | |
| 507704 | 5/1971 | Switzerland . | |
| 0749392 | 7/1980 | U.S.S.R. | 623/19 |
| 1417871 | 8/1988 | U.S.S.R. | 623/22 |

Primary Examiner—David H. Willse
Attorney, Agent, or Firm—Dowell & Dowell

[57] ABSTRACT

A humeral prosthesis including a shank having a metaphyseal part having a housing therein with a semi-spherical portion in which housing is introduced a sphere to which is secured a bearing surface hemispherical cap adapted to be received within the glenoid cavity of a shoulder. A securing element is provided which extends through the metaphyseal part of the shank for securing the sphere within the housing at a predetermined position with respect to the shank.

22 Claims, 7 Drawing Sheets

HUMERAL PROSTHESIS INCORPORATING A SPHERE

BACKGROUND OF THE INVENTION

1. Field of the Invention

The present invention relates to improvements in or relating to prostheses of the upper end of the humerus, of the type comprising a shank which anchors in the humeral channel and a hemispherical cap adapted to cooperate with the glenoid cavity of the shoulder.

The prosthesis according to the invention associated with a prosthetic glenoid cavity allows surgical treatment in particular of the degenerative disorders of gleno-humeral arthrosis, but also that of other disorders. Isolated, the humeral prosthesis according to the invention is intended for broad indications such as cephalo-tuberositary fractures non-accesible for conservative surgery, but also for any painful syndrome of the shoulder associated with an isolated destruction of the humeral head.

2. History of the Related Art

Prostheses intended for such treatments are, of course, already known, such as the so-called NEER prostheses. However, such a prosthesis is monobloc, with the result that it is necessary to have in stock a large number of implants to respond to the anatomical requirements of various patients. Moreover, these prostheses have one size of shank and hemispherical cap, the latter not being able to be offset as is necessary in certain cases. Moreover, this cap has a fixed inclination and it does not satisfactorily cover the plane of cut of the end of the humerus, with the result that the bone must be adapted to the prosthesis, with all the anatomical consequences that this involves.

Swiss document 507 704 also discloses a hip prosthesis shank which comprises at one of its ends a flange provided with a bearing surface intended to rest on the remaining osseous part.

A pivot issues from the flange, defining an angle of inclination with respect to the bearing surface. This pivot is preferably conical and includes on its periphery retaining means such as ribs, teeth, projections or the like.

Different ball-joints may be fixed on this prosthesis shank, which are all secured to a neck provided with a variable inclination. Fixation is effected by means of the pivot and the retaining means.

The use of a plurality of ball-joints makes it possible to define the most favourable angle of inclination, angle of anteversion and the lateral offset of the spherical cap. Such a prosthesis has certain drawbacks concerning the flange which prevents optimum hold of the prosthesis in the metaphysis and greatly reduces the overshoot in space of the spherical cap.

Applicants' French Patent Application No. 2 685 633 also discloses a modular humeral prosthesis comprising elements including a humeral anchoring shank provided with a metaphyseal part formed by an oblique bearing face; a wedge-shaped brace of which one of the end faces fits on the bearing face of the shank; and a hemispherical humeral cap whose base is fixed with respect to the second end face of the brace. This fixation, which is off-center with respect to the geometrical axis of the cap, allows angular adjustment of the latter with respect to the brace. The cap and the shank are locked on the brace in the desired position.

A prosthesis of this type presents certain drawbacks concerning the height of placement of the cap, the indexed but non-continuous adjustment of the inclination of the cap, the offset in the plane of cut of the bone, and the adjustment of the retrotorsion of the cap independently of the position of the shank.

It is an object of the improvements forming the subject matter of the present invention to produce a humeral prosthesis which overcomes the drawbacks set forth hereinabove.

SUMMARY OF THE INVENTION

The humeral prosthesis according to the present invention comprises a humeral shank which is provided in its metaphyseal part with a housing with spherical bottom in which is introduced a sphere provided to receive a hemispherical cap, while screw means allow immobilization thereof in a determined angular position with respect to the axis of the humeral shank.

BRIEF DESCRIPTION OF THE DRAWINGS

The invention will be more readily understood on reading the following description with reference to the accompanying drawings, in which.

DESCRIPTION OF PREFERRED EMBODIMENT

Figure 1:
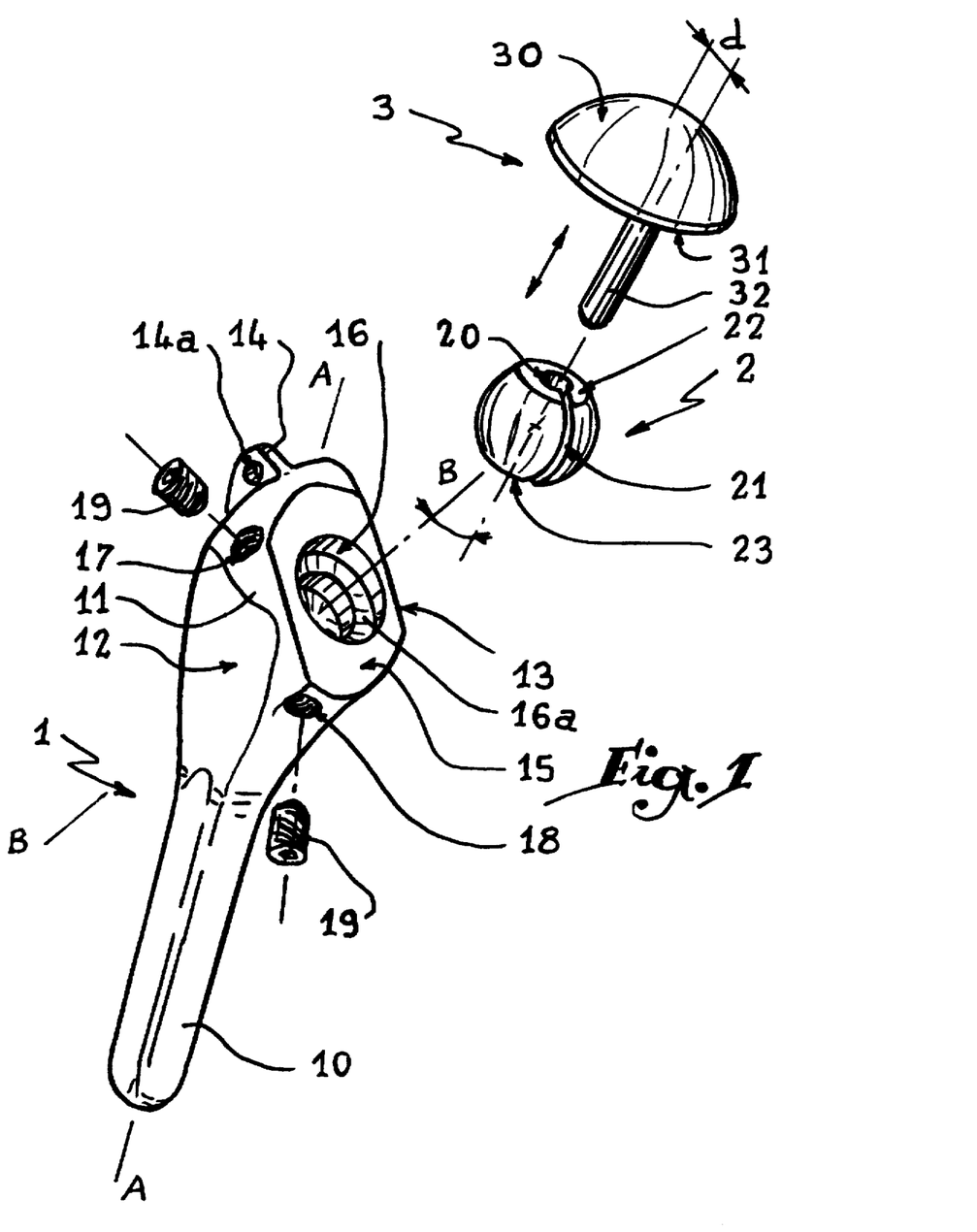
FIG. 1 is an exploded view in perspective illustrating the humeral prosthesis according to the present invention.
Figure 2:
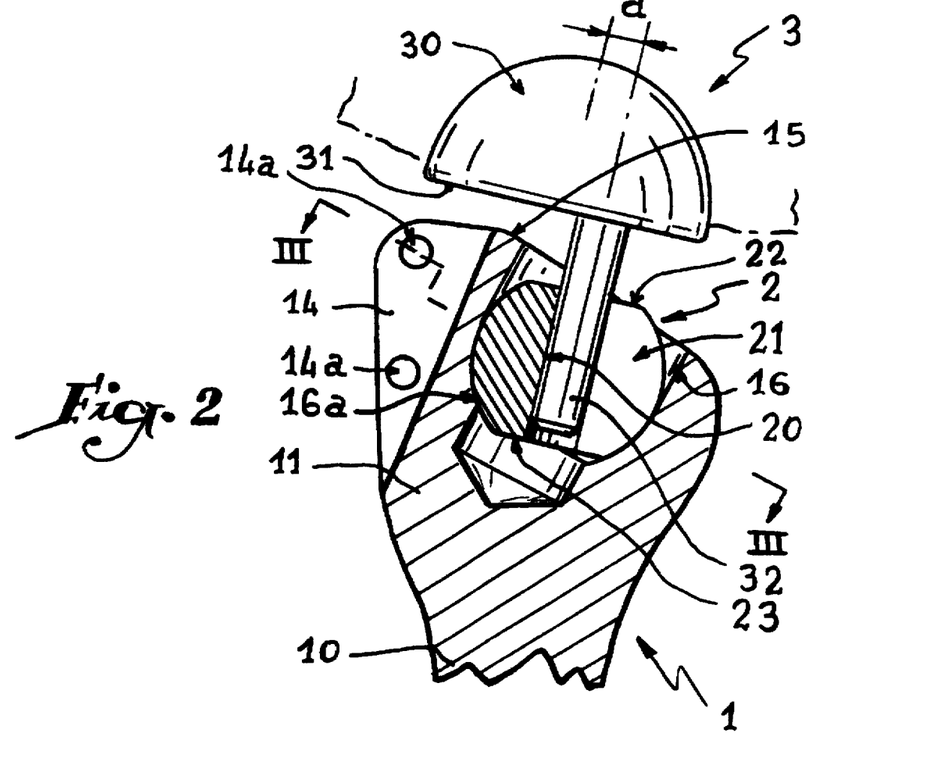
FIG. 2 is a section showing in detail the positioning and holding of the hemispherical cap inside the shank of the humeral prosthesis.

Referring now to the drawings, FIGS. 1 and 2 firstly show the three elements of the modular prosthesis according to the invention, namely a shank 1, a sphere 2 and a hemispherical cap 3.

Shank 1 has an elongated axis A—A comprises a rod 10 of circular section which engages in the humeral channel and a metaphyseal part 11 having a flared profile. In the sagittal plane, the metaphyseal part 11 comprises slightly inclined panels 12 and 13. In addition, the metaphyseal part 11 is provided with one or more ailerons or flanges 14 disposed on the outer and/or lateral face of the rod 10 and which have at least one perforation or opening 14a allowing, in the case of fracture, a reconstitution of the upper end of the humerus around the prosthesis.

Rod 10, and more particularly the metaphyseal part 11, ends in an inclined face 15 with respect to the longitudinal axis of the rod. The inclined face 15 is pierced with a blind housing 16 of cylindrical profile. The bottom of the cylindrical housing 16 has a semi-spherical bearing surface 16a intended to serve as bearing for the sphere 2, as will be seen more readily hereinbelow.

Figure 3:
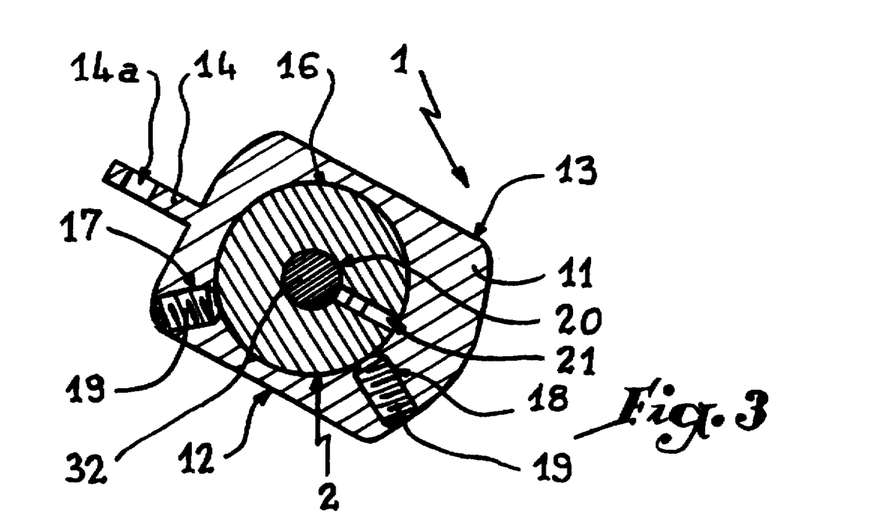
FIG. 3 is a section along III—III (FIG. 2) showing the screwing means for immobilizing the sphere and the cap with respect to the axis of the humeral prosthesis.

The metaphyseal part 11 is pierced with two tapped holes 17, 18 which open inside the cylindrical housing 16 and which are each provided to receive a headless locking screw 19. The axes of holes 17 and 18 are provided to be oblique and inclined with respect to the axis B—B of the housing 16.

The center of sphere 2 is pierced with a bore 20 in which a radial slit 21 opens out, giving a certain elasticity to the sphere. The poles of sphere 2 comprise a flat portion 22, 23 respectively, reducing its size inside the housing 16 of the metaphyseal part 11.

The hemispherical cap 3 has a perfectly polished outer face 30, limited by a base 31. The latter comprises, perpendicularly, a cylindrical pin 32 which is offset laterally by a distance d with respect to its center, thus offering the possibility of off-centering of the cap 3. Moreover, the pin 32 may have a conical outer profile whose smaller diameter lies opposite base 31.

It will be readily understood that, once sphere 2 has been introduced in housing 16 in abutment against the semispherical bearing surface 16a, it suffices to position the hemispherical cap 3 so that pin 32 cooperates with bore 20 of the sphere. The height of pin 32 is sufficient to be able to adjust the distance separating cap 3 with respect to rod 1 of the humeral prosthesis. In addition, sphere 2 allows an angular adjustment of cap 3 in all possible directions with respect to the axis of shank 1. Finally, the lateral offset of pin 32 with respect to the center of base 31 of cap 3 allows a final adjustment about the pin in order to move it out of center so that it can cooperate with the glenoid cavity of the shoulder.

As soon as all the angular adjustments have been made, the surgeon tightens screws 19 inside holes 17 and 18 so that they press against sphere 2 to immobilize it inside housing 16 and deform it radially due to its slit 21 in order to tighten pin 32 inside bore 20. It is ascertained that the points of impact of screws 19 with sphere 2 lie above its principal axes so as to prevent it from rising under forces of traction.

FIGS. 4, 5, 6 and 7 illustrate various embodiments of the modular prosthesis illustrated in FIGS. 1 to 3. In these Figures, the elements corresponding to those of FIGS. 1 to 3 bear the same reference numbers and indices.

Figures 4, 5:
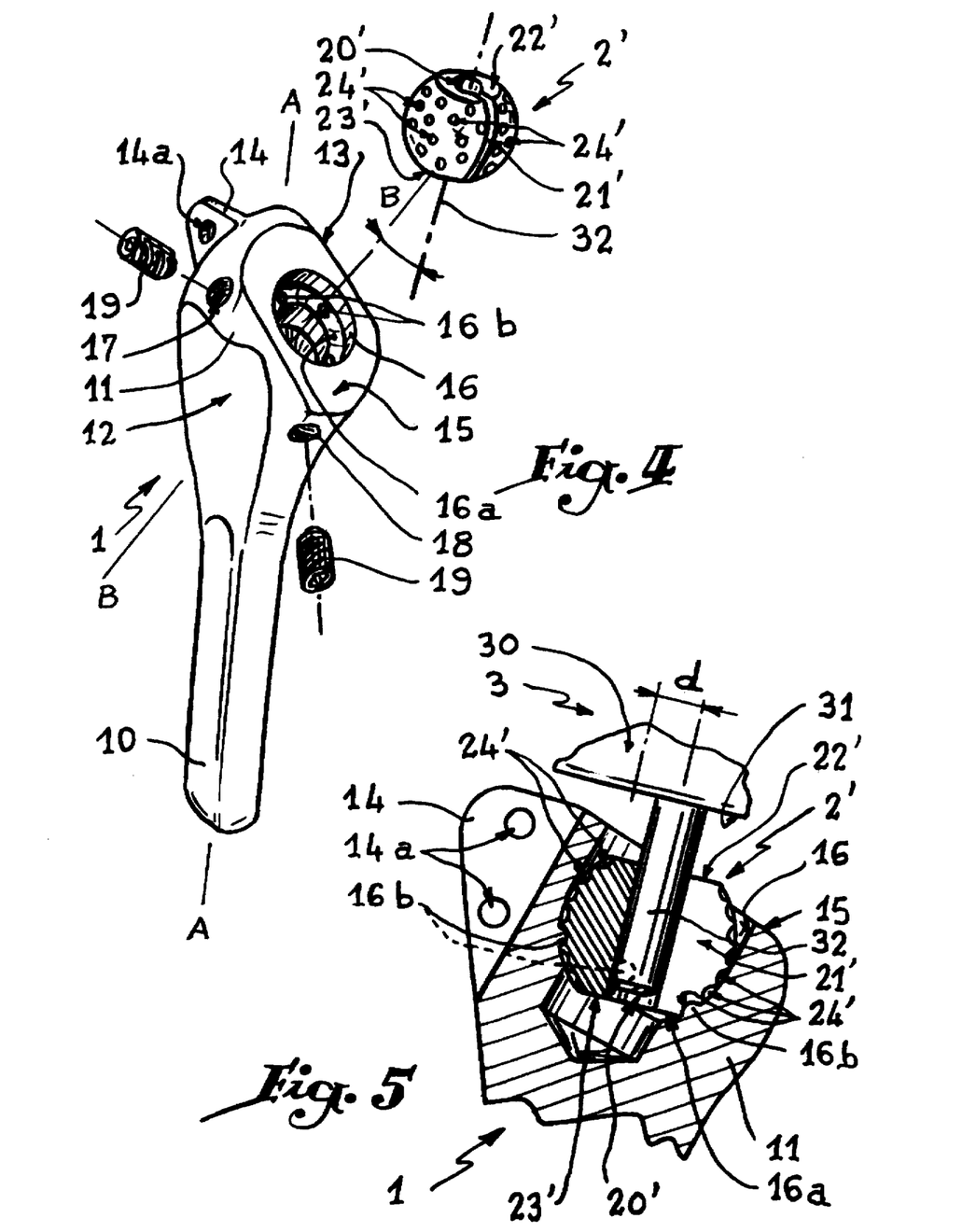
FIGS. 4 and 5 are views illustrating a first variation of the humeral prosthesis according to the invention.

The purpose of the embodiment illustrated in FIGS. 4 and 5 is to provide a sphere 2' presenting a surface state allowing an indexation of each of its positions with respect to the humeral shank 1.

The cylindrical housing 16 provided inside the metaphyseal part 11 of shank 1 includes on its semi-spherical bearing surface 16a parts in relief 16b regularly distributed on the periphery of the circumference of housing 16.

Sphere 2' has a central bore 20' in which a slit 21' opens out, while its surface is covered with a series of cavities 24' in the form of portions of a sphere of diameter substantially identical to those of the elements in relief 16b provided on the spherical bearing surface 16a of housing 16. Sphere 2' likewise comprises at each pole flat portions 22' and 23' reducing its size inside housing 16.

It is ascertained that the cavities 24' cooperate with the elements in relief 16b of housing 16, allowing an angular indexation of the sphere 2' before its immobilization with pin 32 of cap 3 via the locking screws 19.

Figure 6:
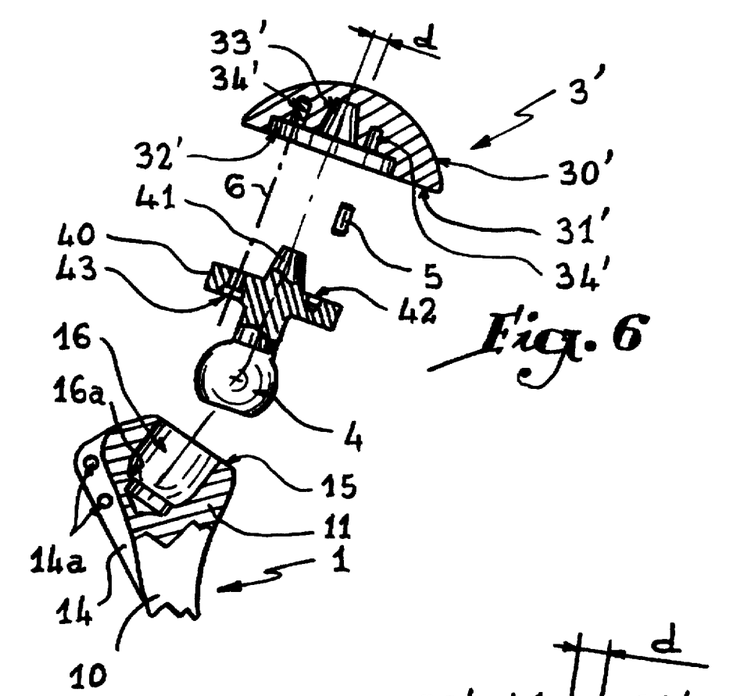
FIGS. 6 and 7 are views showing a second variation of the humeral prosthesis according to the present invention.
Figure 7:
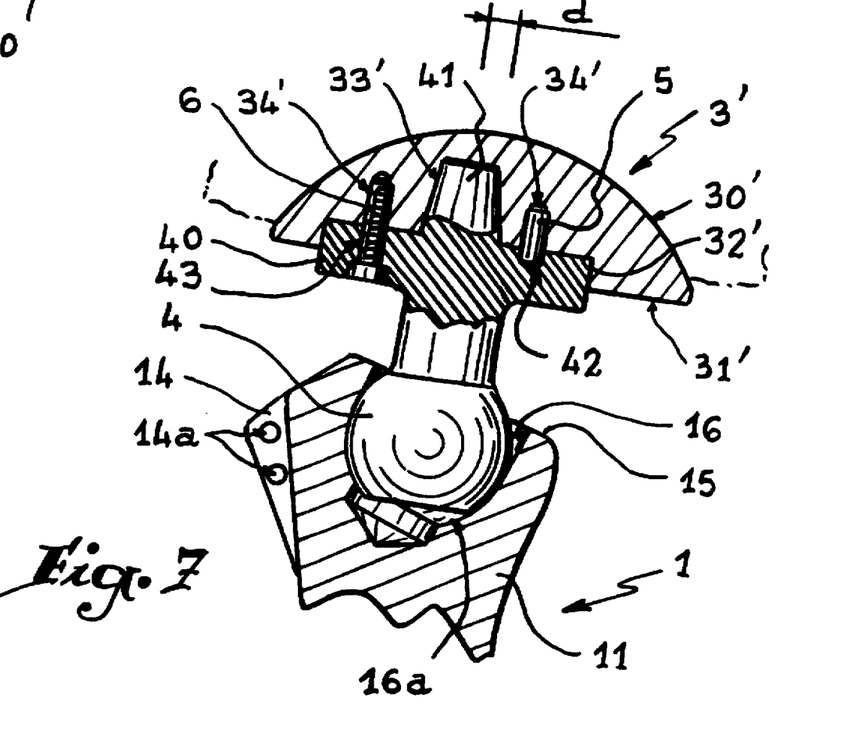

The second varied embodiment illustrated in Figures 6 and 7 is provided to be able to use the spherical caps described in Applicants+ French Patent Application No. 2 685 633.

In fact, the cylindrical housing 16 with semi-spherical bearing surface 16a is provided to receive a sphere 4 secured to a circular flange 40 at the center of which rises a truncated stud 41, to the side of which is made a blind hole 42 intended to receive a pin 5.

Near the truncated stud 41 is provided another stepped through-hole 43 which allows a screw 6 to be placed in position, the use of which will be seen hereinbelow.

A hemispherical cap 3' comprises a perfectly polished outer face 30' limited by a base 31' In the latter, a circular recess 32' has been made off-center, whose diameter corresponds, to within the clearance, to that of the flange 40. At the center of this recess is made a truncated bore 33' whose diameter corresponds to that of stud 41 of flange 40. A series of eight tapped holes 34' is made in the bottom of the recess 32' concentric ally with respect to the center thereof.

The hemispherical cap 3' is assembled on sphere 4 by engagement of stud 41 in bore 33', flange 40 fitting in recess 32' while pin 5 mounted in hole 42 fits in one of the holes 34' Cap 3' is immobilized on sphere 4 by means of screw 6 which cooperates with the corresponding tapped hole 34' after having passed through the stepped hole 43.

The hemispherical cap 3' being mounted on sphere 4, it suffices to fix the assembly on shank 1. To that end, sphere 4 is introduced in the cylindrical housing 16 so as to abut against the semi-spherical bearing surface 16a, while the locking screws 19 are tightened to come into contact with the sphere in order to immobilize it in the desired angular position.

It will be noted that the outer surface of sphere 4 may be covered with a series of cavities identical to those, 24', of sphere 2' to cooperate with the elements in relief 16b of housing 16 in order to allow indexation of the sphere 4 before it is fixed.

FIGS. 8 to 13 show a third varied embodiment of the modular prosthesis according to the invention, enabling the hemispherical caps described in Applicants' French Patent Application No. 2 685 633 to be used.

In FIGS. 8 to 13, the elements corresponding to those of FIGS. 6 and 7 bear the same reference numbers and indices- The humeral prosthesis comprises a shank 1', a sphere 4 and a hemispherical cap 3'

Figure 8:
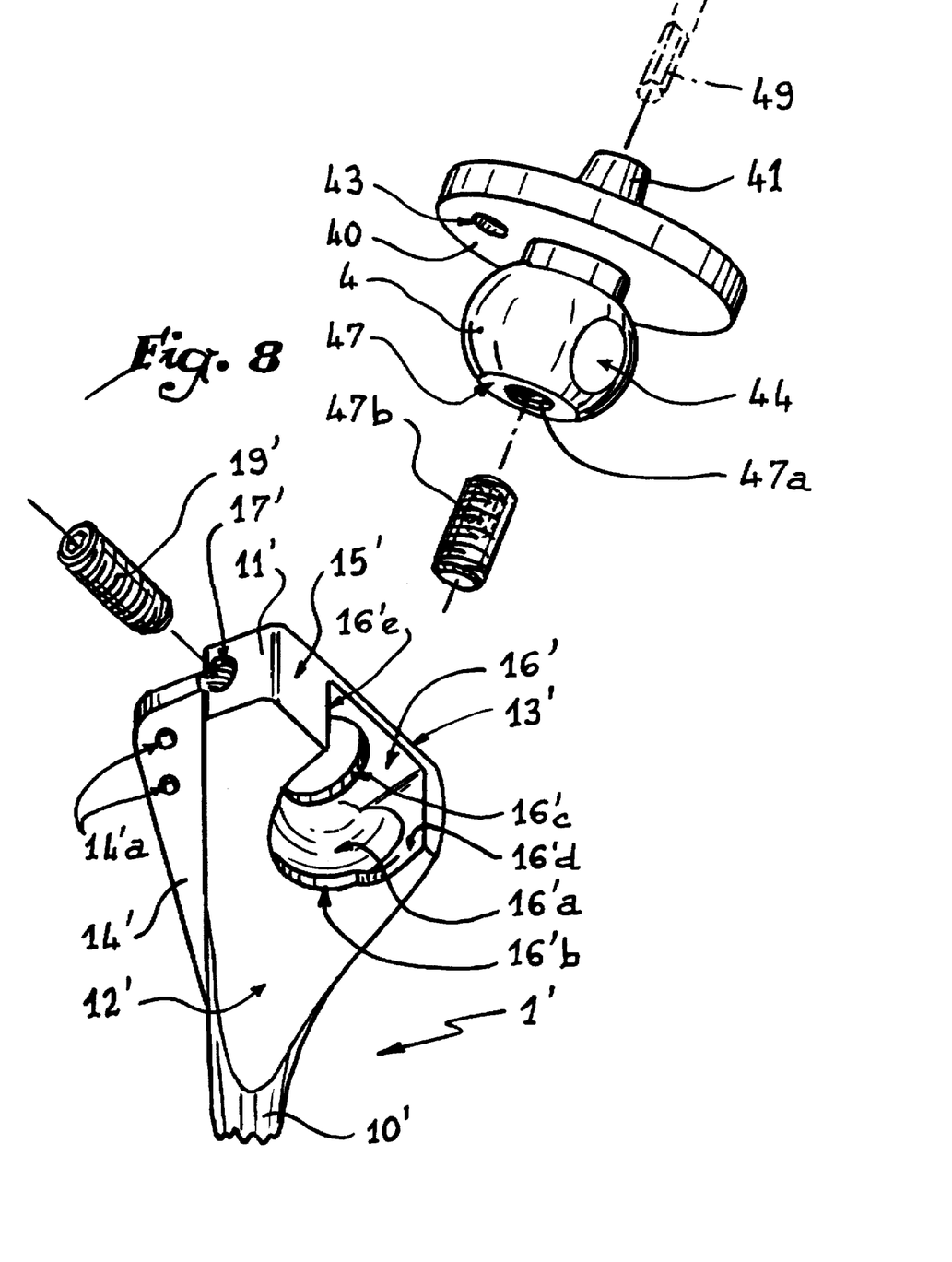
FIGS. 8 to 13 are views showing a third variation of the humeral prosthesis according to the present invention.
Figure 9:
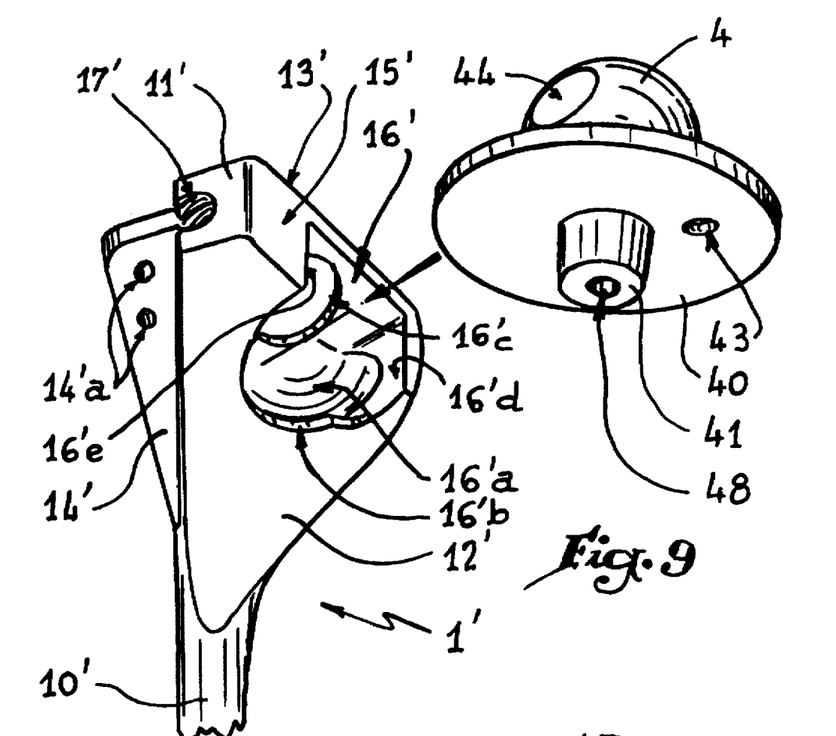

Shank 1' comprises a rod 10' of circular section which engages in the humeral channel and a metaphyseal part 11' having a flared profile. In the sagittal plane, the metaphyseal part 11' comprises slightly inclined panels 12' and 13' In addition, the metaphyseal part 11' is provided with one or more flanges 14' disposed on the outer and/or lateral face of rod 10' and which has at least one perforation 14'a allowing, in the case of a fracture, a reconstitution of the upper end of the humerus around the prosthesis.

Rod 10' and more particularly the metaphyseal part 11' ends in a face 15' inclined with respect to the longitudinal axis of the rod. The inclined face 15' is pierced with a housing 16' presenting a semi-spherical bearing surface 16'a intended to serve as bearing for sphere 4, as will be seen more readily hereinbelow.

In the metaphyseal part 11' and on side 12', a C-shaped opening 16'b is made, opening inside housing 16' Opposite opening 16'b and on side 13' is pierced a hole 16'c opening inside housing 16' This latter comprises, perpendicularly to opening 16'b, two parallel faces 16'd, 16'e which are likewise disposed perpendicularly to the inclined face 15' The distance separating faces 16'd and 16'e is less than the diameter of the spherical bearing surface 16'a. It is ascertained that this latter extends above its principal axes to define a bearing surface of more than a hemi-sphere.

The metaphyseal part 11' is pierced with at least one tapped hole 17' which opens out inside housing 16' and more particularly inside the spherical bearing surface 16'a. Hole 17' is provided to receive a headless locking screw 19' to immobilize sphere 4. The principal axis of hole 17' is provided to be either oblique and inclined with respect to the axis of housing 16', or parallel to those defining the inclined face 15'.

Housing 16' with semi-spherical bearing surface 16'a is provided to receive a sphere 4 secured to a circular flange 40 at the center of which a truncated stud 41 extends, to the side of which a blind hole 42 intended to receive a pin (not shown) is made.

Near the truncated stud 41 there is provided another, stepped through-hole 43 which allows a screw 6 (not shown) to be placed in position.

In addition, sphere 4 presents, on its periphery, flat portions 44, 45 disposed opposite each other. It is observed that the distance separating the two opposite flat portions 44 and 45 is slightly less than that provided between the parallel faces 16'd and 16'e.

The pole of sphere 4 opposite flange 40 is machined to form a flat portion 47 whose center is pierced with a tapped hole 47a.

The taped hole 47a communicates coaxially with a smooth hole 48 which is made in the truncated stud 41 and flange 40. The smooth hole 48 opens to the outside in the upper part of the truncated stud 41 to allow engagement of a key element 49.

The tapped hole 47a is provided to receive a headless locking screw 47b which is actuated by the key element 49 as will be seen more readily hereinbelow.

Cap 3' is positioned and immobilized on sphere 4 by means of screw 6 as has already been described hereinbefore with reference to FIGS. 6 and 7.

The hemispherical cap 3' having been mounted on sphere 4, it suffices to fix the assembly on shank 1' To that end, sphere 4 is introduced in the cylindrical housing 16' so as to abut against the semi-spherical bearing surface 16'a.

Figure 10:
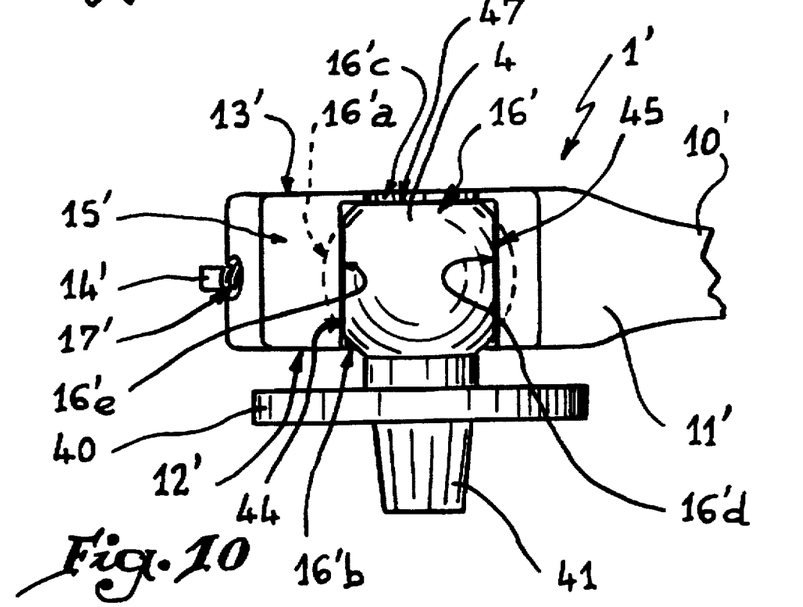

Sphere 4 is positioned and fixed on shank 1' in the following manner: flat portions 44 and 45 are oriented parallel to faces 16'd and 16'e to allow introduction of sphere 4 in housing 16' (FIG. 10).

It will be noted that, in this position, flange 40 is disposed parallel to opening 16'b, while flat portion 47 lies opposite hole 16'c.

Figures 11, 12, 13:
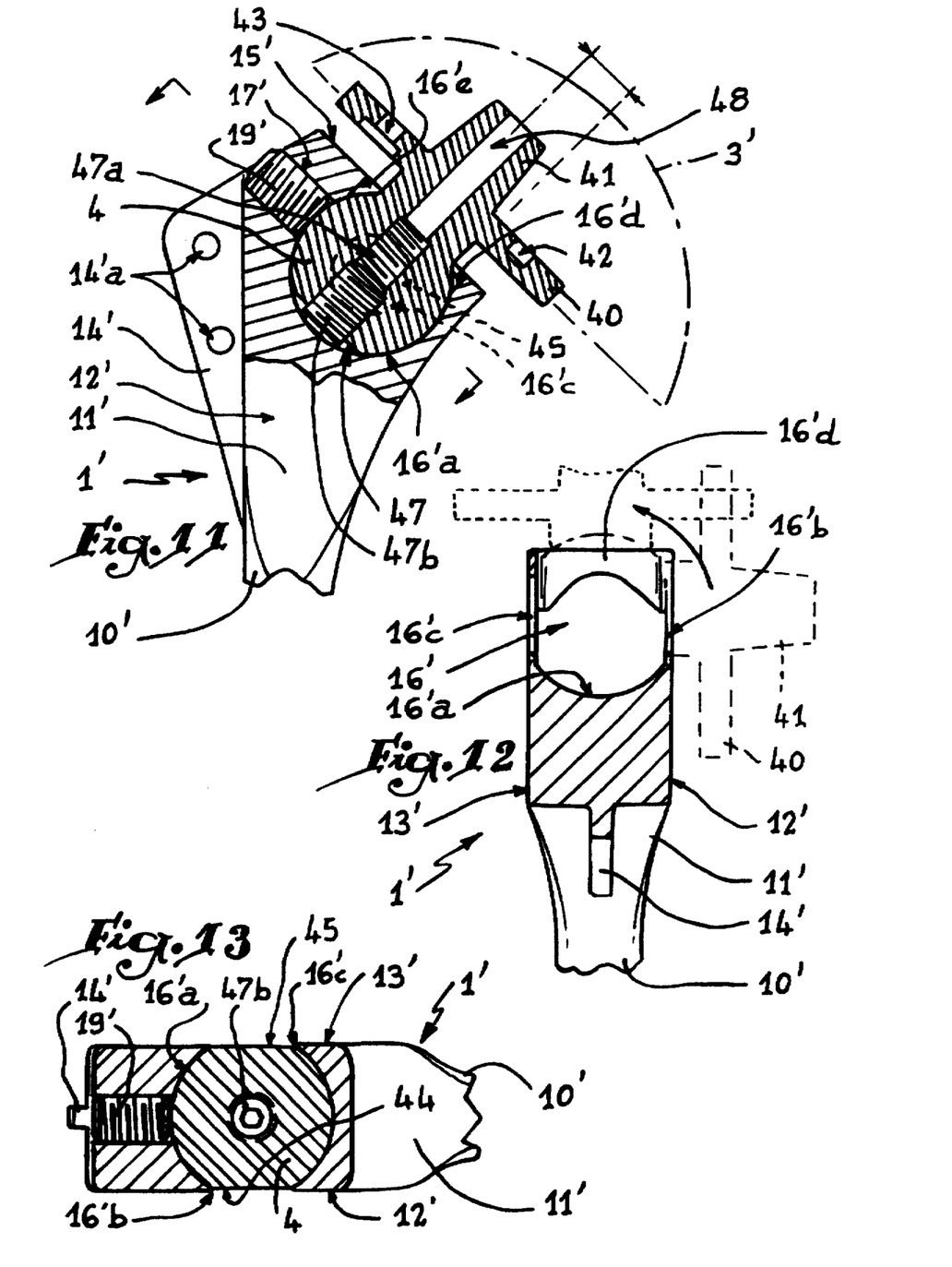

Sphere 4 is then turned inside housing 16' for flange 40 to be placed above the inclined face 15' of shank 1' ( FIG. 12 ).

Sphere 4 is pivoted about its axis for the flat portions 44, 45 to lie respectively opposite opening 16'b and hole 16'c (FIGS. 11, 13).

The locking screws 19' and 47b are tightened in order to immobilize sphere 4 in the desired angular position ( FIGS. 11, 13).

It will be noted that the locking screw 47b is actuated by the key element 49 which traverses stud 41 and flange 40, in order that the screw abuts against the bottom of the semi-spherical bearing surface 16'a. By tightening screw 47b, sphere 4 is applied and blocked on the upper part of the semi-spherical bearing surface 16'a.

Screw 19' comes into contact with the spherical surface to allow sphere 4 to be blocked in rotation about its axis.

It is ascertained that the modular prosthesis according to the invention allows the surgeon to adjust the hemispherical cap 3, 3' in a plurality of different planes with respect to the principal axis of shank 1, 1' so as to correspond perfectly to all anatomies. This type of modular prosthesis avoids having to store a certain number of distance pieces for adjusting the inclination with respect to the axis of the shank.

It must, moreover, be understood that the foregoing description has been given only by way of example and that it in no way limits the domain of the invention which would hot be exceeded by replacing the details of execution described by any other equivalents.

What is claimed is:

1. A prosthesis of the type for use between an upper end of a humerus having a humeral channel and the glenoid cavity of a shoulder wherein the prosthesis comprises, a shank having an elongated axis, said shank being adapted to anchor in the humeral channel, a cap of substantial hemispherical profile adapted to cooperate with the glenoid cavity of the shoulder, said shank having a metaphyseal part with a housing having a semi-spherical bearing surface in which is introduced a sphere to which said cap is mounted, a bore formed through a center of said sphere, at least one radial slit in said sphere and communicating with said bore thereby allowing compression of said sphere along said at least one radial slit, and securing means extending into said housing of said metaphyseal part in a predetermined angular orientation with respect to the elongated axis of said shank for engaging said sphere to secure said sphere within said housing.

2. The prosthesis of claim 1 wherein said sphere includes opposite poles, each pole having a flat portion thereby limiting the size of said sphere inside said housing.

3. The prosthesis of claim 1 wherein said semi-spherical bearing surface has at least one protrusion of a predetermined profile for permitting the angular indexation of said sphere, said sphere having an outer surface having a series of cavities, said cavities having a shape which is complementary to said predetermined profile of said at least one protrusion and said at least one protrusion being engageable within one of said cavities.

4. The prosthesis of claim 3 including a plurality of protrusions extending from said semi-spherical bearing surface, and said cavities being semi-spherical in profile.

5. The prosthesis of claim 1 wherein said shank comprises in said metaphyseal part tapped holes, said securing means including at least one locking screw extending through one of said tapped holes for securing said sphere in said housing.

6. The prosthesis of claim 1 wherein said cap comprises an outer face extending to a base, and a vertical pin extending from said base opposite of said outer face and offset with respect to a center of said base.

7. The prosthesis of claim 6 wherein said pin of said cap is adjustably received within said bore to thereby allow position adjustment of said hemispherical cap with respect to said shank.

8. The prosthesis of claim 1 wherein said housing includes a generally cylindrical portion extending from said bearing surface.

9. The prosthesis of claim 1 wherein the said cap comprises an outer face and a base in which an off-center circular recess is formed, a truncated bore in said recess and a plurality of holes in said base which are concentrically oriented around said truncated bore.

10. The prosthesis of claim 9 wherein said sphere is secured to a circular flange which engages in said off-center recess in said base of said cap, a truncated stud extending from said flange which is engageable in said truncated bore in said recess, and a locking means extending through one of said plurality of holes to secure said cap to said flange.

11. The prosthesis of claim 10 wherein said sphere includes a tapped hole therein which communicates with a through-hole provided in said truncated stud extending from said flange, and a screw element mounted within said tapped hole for selective adjustment to secure said sphere within said housing, whereby a tool may be inserted through said through-hole to engage with said screw element.

12. The prosthesis of claim 1 which said shank includes at least one flange extending outwardly from said metaphyseal part, and at least one opening in said flange.

13. A prosthesis of the type for use between an upper end of a humerus having a humeral channel and the glenoid cavity of a shoulder, wherein the prosthesis comprises, a shank having an elongated axis, said shank being adapted to anchor in the humeral channel and a cap of substantial hemispherical profile adapted to cooperate with the glenoid cavity of the shoulder, said shank having a metaphyseal part with a housing having a semi-spherical bearing surface in which is introduced a sphere to which said cap is mounted, and securing means extending into said housing of said metaphyseal part in a predetermined angular orientation with respect to the elongated axis of said shank for securing the said sphere within said housing, said housing including a C-shaped opening, a hole in said metaphyseal part opposite said C-shaped opening, two parallel faces oriented perpendicularly to said hole and said C-shaped opening and extending from said semi-spherical bearing surface, and said semi-spherical bearing surface being between said hole and said C-shaped opening.

14. The prosthesis of claim 13 wherein said sphere has a diameter, said two parallel faces are spaced at a distance which is less than the diameter of said sphere.

15. The prosthesis of claim 13 wherein said sphere has an outer surface, said bearing surface defining a surface of greater proportion than one half of the outer surface of said sphere.

16. The prosthesis of claim 15 wherein said sphere comprises at least two flat portions which are disposed parallel to each other.

17. The prosthesis of claim 16 wherein said metaphyseal part of said shank includes opposite outer faces which are spaced relative to one another, said flat portions of said sphere being spaced at a distance which is less than the distance at which said opposite faces of said metaphyseal part are spaced.

18. A prosthesis of the type for use between an upper end of a humerus having a humeral channel and the glenoid cavity of a shoulder, wherein the prosthesis comprises, a shank having an elongated axis, said shank being adapted to anchor in the humeral channel, a cap of substantial hemispherical profile adapted to cooperate with the glenoid cavity of the shoulder, said shank having a metaphyseal part with a housing having a semi-spherical bearing surface in which is introduced a sphere to which said cap is mounted, at least one protrusion forming a portion of said bearing surface and having a predetermined profile extending outwardly into said housing, said sphere having an outer surface having a plurality of spaced cavities therein, each of said plurality of cavities having a shape which is complementary to said predetermined profile of said at least one protrusion, said sphere being selectively indexable within said housing so as to selectively align said at least one protrusion to cooperatively engage within one of said plurality of cavities in an indexed position of said sphere, and securing means extending into said housing of said metaphyseal part in a predetermined angular orientation with respect to the elongated axis of said shank for engaging said sphere to secure said sphere within said housing in said indexed position.

19. The prosthesis of claim 18 including a plurality of protrusions extending from and forming portions of said semi-spherical bearing surface, and said cavities being semi-spherical in profile.

20. The prosthesis of claim 18 wherein said cap comprises an outer face extending to a base, and a vertical pin extending from said base opposite of said outer face and offset with respect to a center of said base, said pin of said cap being adjustably received within a bore of said sphere to thereby allow position adjustment of said hemispherical cap with respect to said shank.

21. The prosthesis of claim 18 wherein the said cap comprises an outer face and a base in which an off-center circular recess is formed, a truncated bore in said recess and a plurality of holes in said base which are concentrically oriented around said truncated bore.

22. The prosthesis of claim 21 wherein said sphere is secured to a circular flange which engages in said off-center recess in said base of said cap, a truncated stud extending from said flange which is engageable in said truncated bore in said recess, and a locking means extending through one of said plurality of holes to secure said cap to said flange.

\* \* \* \* \*